US010548605B2

(12) United States Patent
Anderson et al.

(10) Patent No.: US 10,548,605 B2
(45) Date of Patent: Feb. 4, 2020

(54) DETACHABLE IMPLANTABLE DEVICES

(71) Applicant: Boston Scientific Scimed, Inc., Maple Grove, MN (US)

(72) Inventors: James M. Anderson, Corcoran, MN (US); David Raab, Minneapolis, MN (US); Derek C. Sutermeister, Ham Lake, MN (US); Cass Alexander Hanson, St. Paul, MN (US); Timothy A. Ostroot, Cokato, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 417 days.

(21) Appl. No.: 15/015,858

(22) Filed: Feb. 4, 2016

(65) Prior Publication Data

US 2016/0228123 A1 Aug. 11, 2016

Related U.S. Application Data

(60) Provisional application No. 62/112,299, filed on Feb. 5, 2015.

(51) Int. Cl.
*A61B 17/12* (2006.01)

(52) U.S. Cl.
CPC .... *A61B 17/12013* (2013.01); *A61B 17/1214* (2013.01); *A61B 17/12113* (2013.01);
(Continued)

(58) Field of Classification Search
CPC ........ A61B 17/12013; A61B 17/12145; A61B 17/12113; A61B 17/1214; A61B 17/12109; A61B 2017/12054; A61B 17/12022; A61B 17/12118; A61B 17/12104; A61B 2017/1205; 2017/12077; A61B 2017/12081; A61B 2017/12086;
(Continued)

(56) References Cited

U.S. PATENT DOCUMENTS 5,250,071 A 10/1993 Palermo
5,304,195 A 4/1994 Twyford, Jr. et al.
(Continued)

OTHER PUBLICATIONS

Communication pursuant to Article 94(3) EPC for application No. 1670845.2, dated Feb. 7, 2019, 6 pages.

*Primary Examiner* — Erich G Herbermann

(57) ABSTRACT

In some aspects, the present disclosure provides a delivery device for delivering a detachable medical implant that comprises an elongated delivery member and a first engagement portion. The first engagement portion comprises a first proximal-facing surface, a first distal-facing surface, and a first lumen that is configured to accommodate an activation wire, wherein at least 50% of a surface area of the first proximal-facing surface is angled away from a proximal end of the first engagement portion. In other aspects, the present disclosure provides a medical delivery system comprising: such a delivery device; an implantable device comprising a medical device portion and a second engagement portion, the second engagement portion comprising a second lumen configured to accommodate an activation wire, a second proximal-facing surface and a second distal-facing surface; and an activation wire. Other aspects pertain to methods of medical device delivery using such a medical delivery system.

9 Claims, 2 Drawing Sheets

(52) U.S. Cl.
CPC .. *A61B 17/12145* (2013.01); *A61B 17/12109* (2013.01); *A61B 2017/12054* (2013.01)

(58) Field of Classification Search
CPC .. A61B 2017/1209; A61B 2017/12095; A61B 2017/12059
See application file for complete search history.

(56) References Cited

U.S. PATENT DOCUMENTS

| | | | |
|---|---|---|---|
| 5,925,059 A * | 7/1999 | Palermo | A61B 17/12022 606/191 |
| RE37,117 E | 3/2001 | Palermo | |
| 8,007,509 B2 * | 8/2011 | Buiser | A61B 17/12022 606/108 |
| 2006/0276834 A1 * | 12/2006 | Balgobin | A61B 17/12022 606/200 |
| 2007/0010849 A1 * | 1/2007 | Balgobin | A61B 17/12022 606/200 |
| 2007/0282373 A1 * | 12/2007 | Ashby | A61B 17/0057 606/213 |
| 2008/0208329 A1 | 8/2008 | Bishop et al. | |
| 2008/0300616 A1 | 12/2008 | Que et al. | |
| 2009/0043331 A1 | 2/2009 | Buiser et al. | |
| 2011/0028995 A1 | 2/2011 | Miraki et al. | |
| 2011/0313447 A1 | 12/2011 | Strauss et al. | |
| 2012/0046687 A1 | 2/2012 | Trommeter et al. | |

* cited by examiner

DETACHABLE IMPLANTABLE DEVICES

RELATED APPLICATION INFORMATION

This application claims priority to, and the benefit of, U.S. Patent Application No. 62/112,299, filed on Feb. 5, 2015, which is incorporated by reference in its entirety.

BACKGROUND

The endovascular treatment of a variety of conditions throughout the body is an increasingly more important form of therapy. One such procedure uses embolization coils to occlude a target site by forming a physical barrier to blood flow and/or by promoting thrombus formation at the site. Such treatments can be useful where it is desired to reduce vascularization, including treatments for aneurisms and cancer.

Coils have typically been placed at the desired site within the vasculature using a catheter and a delivery device such as a pusher member. As a first step, a flexible, small diameter catheter can be guided to the target site through the use of a guidewire or by other means. Once the site has been reached, the catheter lumen is cleared by removing the guidewire (if a guidewire has been used), and the coil is placed into the proximal open end of the catheter and advanced through the catheter via the delivery device, which has a distal end that is adapted to engage and push the coil through the catheter lumen as the delivery device is advanced through the catheter. When the coil reaches the distal end of the catheter, it is discharged from the catheter by the delivery device into the vascular site.

Several techniques have been developed to enable more accurate placement of coils within a vessel, including techniques where the delivery device is temporarily affixed to the coil, and which can be released via electrical (e.g., electrolytic dissolution) and mechanical means (e.g., interlocking members operated by an activation wire).

The present disclosure pertains to improved devices, systems and methods for implantable device delivery.

SUMMARY

In accordance some aspects, the present disclosure provides a delivery device for delivering a detachable medical implant that comprises an elongated delivery member and a first engagement portion. The first engagement portion comprises a first proximal-facing surface, a first distal-facing surface, and a first lumen that is configured to accommodate an activation wire, wherein at least 50% (in some embodiments, at least 75%, at least 90%, at least 95%, or more) of a surface area of the first proximal-facing surface is angled away from (e.g., relative to an imaginary plane oriented normal to an axis of the first lumen) a proximal end of the first engagement portion. For example, at least 50%, at least 75%, at least 90%, at least 95%, or more, of the surface area of the first proximal-facing surface may curve away from (e.g., relative to an imaginary plane oriented normal to an axis of the first lumen) the proximal end of the first engagement portion as one moves toward an outer edge of the first proximal-facing surface. As another example, at least 50%, at least 75%, at least 90%, at least 95%, or more, of the surface area of the first proximal-facing surface may slope away from (e.g., relative to an imaginary plane oriented normal to an axis of the first lumen) the proximal end of the first engagement portion in a linear fashion, as one moves toward an outer edge of the first proximal-facing surface.

In various embodiments, which may be used in combination with the above aspects, at least 50% of the surface area of the first proximal-facing surface is curved. For example, the first proximal-facing surface may comprise a portion of a spheroidal surface. In certain cases, the first engagement portion may comprise a spheroid or a portion of a spheroid, within which is formed the first lumen and which provides the first proximal-facing surface and the first distal-facing surface. In these cases, for example, (a) the elongated delivery member may be attached to a portion of a circumference of the spheroid and a plane passing through the circumference may be normal to an axis of the first lumen and/or (b) at least a portion of a length of the elongated member may comprise a first longitudinally sliced portion of a first hollow cylinder and the spheroid may be disposed in a concave side of the first longitudinally sliced portion.

In various embodiments, which may be used in combination with the above aspects and embodiments, the engagement portion may comprise a portion of a hollow cylinder.

In various embodiments, which may be used in combination with any of the above aspects and embodiments, the elongated delivery member may be a tubular delivery member that is adapted to receive the activation wire.

In accordance other aspects, the present disclosure provides a medical delivery system comprising: (a) a delivery device in accordance with any of the above aspects and embodiments, (b) an implantable device comprising a medical device portion and a second engagement portion, the second engagement portion comprising a second lumen, a second proximal-facing surface and a second distal-facing surface, and (c) an activation wire. In these aspects, the activation wire is configured (i) to simultaneous occupy the first and second lumens thereby holding the first and second engagement portions in the coupled state, and (ii) to be removed from the first and second lumens thereby releasing the first and second engagement portions from the coupled state. Typically, when in the coupled state, the first distal-facing surface engages the second proximal-facing surface when the medical device is pushed distally by the elongated delivery member and the first proximal-facing surface engages the second distal-facing surface when the medical device is pulled proximally by the elongated delivery member.

In various embodiments, which may be used in combination with the above aspects and embodiments, the second engagement portion may comprise a spheroid or a portion of a spheroid, within which is formed the second lumen and which provides the second distal-facing surface. In certain of these embodiments, the medical device may comprise a second longitudinally sliced portion of a second hollow cylinder, the spheroid may be disposed in a concave side of the second longitudinally sliced portion, a proximal end of the medical device portion may also be disposed in the concave side of the second longitudinally sliced portion, and the spheroid may be longitudinally spaced from the medical device portion by a gap within which the first engagement portion is positioned when the first and second engagement portions are in the coupled state.

In various embodiments, which may be used in combination with the above aspects and embodiments, the first and second engagement portions may comprise complementary surfaces. In certain of these embodiments, the first and second engagement portion may form a hollow cylinder when in the coupled state.

In various embodiments, which may be used in combination with the above aspects and embodiments, the medical device portion may comprise a vascular occlusion device (e.g., an embolic coil, etc.).

In accordance yet other aspects, the present disclosure provides a method of implanting an implantable device in a subject comprising (a) inserting a medical system in accordance with any of the above aspects and embodiments into a subject when in the coupled state and (b) withdrawing the activation wire from the first and second lumens such that the implantable device is released in the subject.

An advantage associated with delivery devices described herein is that they are resistant to engagement with (e.g., snagging) tissue or a previously implanted device upon removal of the delivery devices from a subject.

DETAILED DESCRIPTION

Figure 1A:
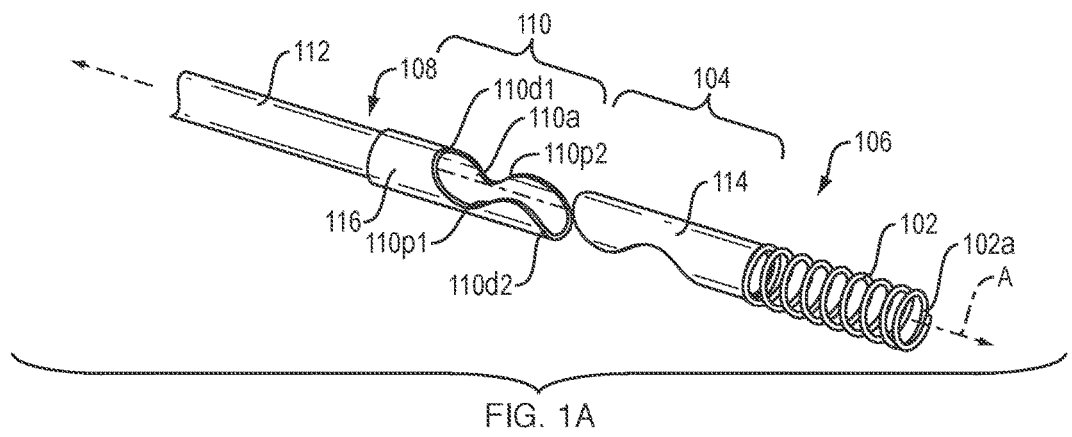
FIG. 1A is a schematic illustration of a distal portion of a delivery device and a proximal portion of an implantable device in accordance with an embodiment of the present disclosure.

A more complete understanding of the present disclosure is available by reference to the following detailed description of numerous aspects and embodiments of the disclosure. The detailed description which follows is intended to illustrate but not limit the disclosure.

As used herein, the terms "proximal" and "distal" generally refer to the relative position, orientation, or direction of an element or action, from the perspective of a clinician using the medical device, relative to one another. Thus, "proximal" may generally be considered closer to the clinician or an exterior of a patient, and "distal" may generally be considered to be farther away from the clinician, along the length or beyond the end of the medical device.

Disclosed herein are delivery devices, systems and methods for delivering an implantable device to a target site, in particular, a detachable, implantable device. The systems include a delivery device and implantable device which can be held in a coupled arrangement by insertion of an activation wire and released from one another by removal of the activation wire. Discussed below are a variety of coupling configurations which include features adapted to inhibit unwanted interaction between the delivery device and the delivery environment (including tissue, previously placed devices, etc.) when retracting the delivery device after delivery.

In accordance with various aspects of the present disclosure, delivery devices are provided which comprise (a) an elongated delivery member, for example, an elongated tube or elongated rod (e.g., a stiff wire), and (b) an engagement portion having a proximal end and a distal end and comprising a lumen that is configured to accommodate an activation wire. The engagement portion also comprises a proximal-facing surface and a distal-facing surface, wherein at least 50% of the proximal-facing surface area of the engagement portion is angled away from the proximal end of the engagement portion. For example, at least 50%, at least 60%, at least 70%, at least 80%, at least 90%, at least 95%, or more, of the proximal-facing surface area of the engagement portion may be angled away from the proximal end of the engagement portion. This feature is advantageous, for example, in that when the delivery device is ultimately withdrawn proximally after delivery of the implantable device, is resistant to engagement with another object (e.g., tissue, a previously implanted device, etc.).

In certain embodiments, at least 50% of the proximal-facing surface area of the first engagement portion is curved. For example, at least 50%, at least 60%, at least 70%, at least 80%, at least 90%, at least 95%, or more, of the proximal-facing surface area of the engagement portion may be curved.

In accordance with various aspects of the present disclosure, medical systems are provided which comprise a delivery device, an implantable device and an activation wire configured to reversibly couple the implantable device and delivery device together. The delivery device comprises an elongated delivery member, for example, an elongated tube or elongated rod, and a first engagement portion having a proximal end and a distal end and comprising a first lumen, a first proximal-facing surface and a first distal-facing surface, wherein at least 50% of the proximal-facing surface area of the first engagement portion is angled away from the proximal end of the first engagement portion. For example, at least 50%, at least 60%, at least 70%, at least 80%, at least 90%, at least 95%, or more, of the proximal-facing surface area of the first engagement portion may be angled away from the proximal end of the first engagement portion. The implantable device includes a medical device portion (e.g., an occlusion device such as an embolization coil, etc.) and a second engagement portion comprising a second lumen, a second proximal-facing surface and a second distal-facing surface.

Moreover, the first and second engagement members may be configured to form a coupled state in which the first and second lumens are aligned, in which at least one first distal-facing surface of the first engagement portion engages at least one second proximal-facing surface engagement portion when the medical device is pushed distally by the elongated delivery member, and in which at least one first proximal-facing surface of the first engagement portion engages at least one second distal-facing surface of the second engagement portion when the medical device is pulled proximally by the elongated delivery member.

Prior to delivery of the implantable device, the first and second engagement portions are bought together and the activation wire is simultaneously disposed within the first and second lumens of the first and second engagement portions, forming a delivery system in which the devices are reversibly coupled, with decoupling being accomplished by withdrawal of the activation wire. Thus, the activation wire is configured to simultaneous occupy the first and second lumens and hold the first and second engagement portions in the coupled state during delivery and is further configured to be removed from the first and second lumens and release the first and second engagement portions from the coupled state.

In one embodiment, such a delivery system be employed to place one or more coils or other implantable device(s) at a target site within the vasculature using a flexible, small diameter catheter. As a first step, the catheter can be guided to the target site through the use of a guidewire or by other means. Once the site has been reached, the catheter lumen is cleared by removing the guidewire (if a guidewire has been used) and the distal end of the system (i.e., the distal end of the medical device portion, e.g., the distal end of a coil) is placed into a proximal open end of the catheter and advanced through the catheter via the delivery member. Once the implantable device emerges from the distal end of the catheter and is positioned at the desired target site, the activation wire may be withdrawn, allowing the first and second engagement portions to disengage, thereby releasing the medical device at the vascular site. Because the first engagement portion described herein is designed such that essentially all of the proximal-facing surface area of the first engagement portion is angled away from the proximal end of the first engagement portion, withdrawal of the first engagement portion from the vasculature and into the catheter is facilitated.

In certain embodiments, the medical device portion may comprise a vascular occlusion device, such as an embolic coil or other occlusion device. Where the medical device portion is an embolic coil, it may be formed from metals or alloys, for example, selected from platinum group metals, particularly platinum, rhodium, palladium, and rhenium, as well as tungsten, gold, silver, tantalum, and alloys of these metals including platinum/tungsten alloy. These materials have significant radiopacity, and their alloys may be tailored to have a blend of flexibility and stiffness for the coil. They are also generally biologically inert. The coil may also include shape memory components, such as nitinol components, among others.

In certain embodiments, the elongated delivery member may be a solid elongated member (e.g., a solid rod, also referred to herein as a wire) or may be a tubular delivery member having a lumen. Where the elongated delivery member is a tubular delivery member, the lumen may be adapted to receive the activation wire.

The elongated delivery member may be made using a variety of biocompatible materials. Beneficial materials for forming the elongated delivery member include metals (including pure metals and metal alloys), for example, selected from stainless steel (e.g., 303, 304v, or 316L stainless steel), nickel-titanium alloy (nitinol) (e.g., super elastic or linear elastic nitinol), nickel-chromium alloy, nickel-chromium-iron alloy, cobalt alloy, nickel, titanium, platinum, and the like. Beneficial materials for forming the elongated delivery member further include stiff polymers such as polycarbonates, polyamides (e.g., nylons, etc.), parylene coatings or layers, and the like. In some embodiments, the elongated delivery member may be formed from a combination of polymeric and inorganic (e.g., metals, ceramics, etc.) materials.

The engagement portions may also be made using a variety of biocompatible materials. Beneficial materials for forming the engagement portions include those materials listed above for forming the elongated delivery member, among others.

It will be appreciated that the various components of the disclosure including the engagement portions can be formed from or may include a radiopaque material. One skilled in the art will appreciate that a variety of imaging capable materials can be used, including, for example, materials detectable with, x-ray, including fluoroscopy, MRI, CT, PET, SPECT, and combinations thereof.

In certain embodiments, the first and second engagement portions may comprise complementary surfaces. In certain embodiments, the first and second engagement portions may each comprise a portion of a hollow cylinder and may have complementary surfaces that engage one another to form a hollow cylinder.

One embodiment of the disclosure will now be described in conjunction with FIGS. 1A-1C. Turning to FIG. 1A, there is schematically illustrated therein a distal portion of a delivery device 108 and a proximal portion of an implantable device 106.

The delivery device 108 comprises an elongated delivery member 112, specifically, an elongated tubular delivery member. The delivery device 108 also comprises a first engagement portion 110 comprising a lumen 110 $a$, at least one first proximal-facing surface (specifically two first proximal-facing surfaces 110 $p$ 1, 110 $p$ 2) and at least one first distal-facing surface (specifically two first distal-facing surfaces 110 $d$ 1, 110 $d$ 2). As can be seen substantially all of the proximal-facing surface area (i.e., the combined surface area of 110 $p$ 1 and 110 $p$ 2) of the first engagement portion 110 is angled away from the proximal end (i.e., angled toward the end that is opposite the delivery device 108) of the first engagement portion 110. As previously noted, this is advantageous in that, when the delivery device 108 is ultimately withdrawn proximally after delivery of the implantable device, it is less likely to engage another object (e.g., tissue or a previously implanted device). As also can be seen substantially all of the proximal-facing surface area is curved. The surfaces 110 $p$ 1, 110 $p$ 2, 110 $d$ 1, 110 $d$ 2 are provided by first engagement member 116 in the embodiment shown.

The implantable device 106 includes a medical device portion 102, in particular, an occlusion device such as an embolization coil (only a proximal portion of the embolization coil is illustrated) having a coil lumen 102$a$ and a second engagement portion 104, which is complementary to the first engagement portion 110. Seen in FIGS. 1A and 1C, like the first engagement portion 110, the second engagement portion 104 comprises at least one second distal-facing surface (specifically, two second distal-facing surface 104$d$1, 104$d$2) and at least one second proximal-facing surface (specifically, two second proximal-facing surfaces 104$p$1, 104$p$2). The second engagement portion 104 also comprises a lumen 104$a$. The lumen 104$a$ and surfaces 104$p$1, 104$p$2, 104$d$1, 104$d$2 are provided by a second engagement member 114, which is shown separately in FIG. 1C. Although the second engagement member 114 is essentially a mirror image of the first engagement member 116, this is not required, as a wide variety of asymmetric configurations possible.

Figure 1B:
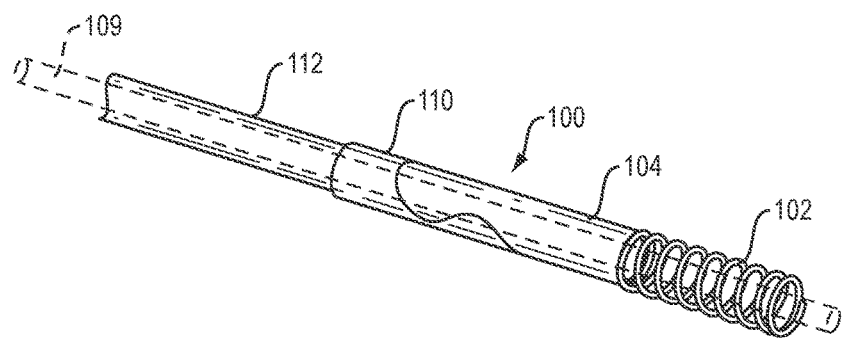
FIG. 1B is a schematic illustration of a delivery system wherein the delivery device and implantable device shown in FIG. 1A are coupled and held together via an actuation wire.

Prior to delivery, the first and second engagement portions 110, 104 are bought together as shown in FIG. 1B and an activation wire 109 (a portion of which is shown in phantom) is simultaneously positioned within the first and second lumens 110$a$, 104$a$ such that the devices are reversibly coupled. In particular, in the embodiment shown, the activation wire 109 simultaneously occupies a lumen of the delivery tube 112, the first engagement portion lumen 110$a$, the second engagement portion lumen 104$a$, and a portion of the coil lumen 102$a$ (this is optional as it is not necessary for coupling). Because the first engagement portion 110 has at least one proximal-facing surface (i.e., 110$p$1, 110$p$2) that can engage at least one distal-facing surface (i.e., 104$d$1, 104*d*2) of the second engagement portion 104, when the elongated delivery member 112 of the delivery device 108 is pulled in a proximal direction, the first engagement portion 110 will engage and pull the second engagement portion 104 in a proximal direction. Analogously, because the first engagement portion 110 has at least one distal-facing surface (i.e., 110*d*1, 110*d*2) that can engage at least one proximal-facing surface (i.e., 104*p*1, 104*p*2) of the second engagement portion 104, when the elongated delivery member 112 of the delivery device 108 is pushed in a distal direction, the first engagement portion 110 will engage and push the second engagement portion 104 in a distal direction. It should be noted that while the first and second engagement portions 110, 104, have two pairs of surfaces that can potentially engage when the delivery device 108 is pushed in a distal direction and pulled in a proximal direction, one pair of surfaces is sufficient for each direction.

It should also be noted that the coil 102 and second engagement member 114 may be formed from a single piece of material or from different pieces of material. Similarly, the elongated delivery member 112 and first engagement member 116 may be formed from a single piece of material or from different pieces of material. In this regard, various materials described herein may be attached using a variety of suitable techniques, for example, soldering, welding, adhering (e.g., with adhesive), and/or mechanically mating the materials together.

Figure 1C:
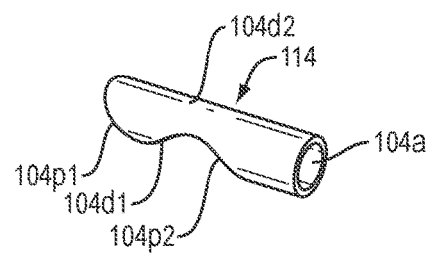
FIG. 1C is a schematic illustration of a portion of the implantable device of FIG. 1A.

Once the first and second engagement portions 110, 104 are paired as shown in FIG. 1C and the activation wire 109 is introduced through the lumens 110*a* and 104*a* of the first and second engagement portions 110, 104, then first and second engagement portions 110, 104 will remained coupled until the activation wire 109 is removed, at which point the first and second engagement portions 110, 104 are released from one another.

As will be appreciated by those skilled in the art upon viewing FIG. 1A, when the delivery tube 112 and first engagement member 116 are separate entities, the first engagement portion lumen 110*a* may be provided by either the distal end of the delivery tube 112 or the first engagement member 116, or both. Similarly, when the second engagement member 116 and coil 102 are separate entities, the second engagement portion lumen 104*a* may be provided by the second engagement member 116, a proximal portion of the coil 102, or both.

In the embodiments shown in FIGS. 1A-1C, first and second engagement members 116, 114 comprise complementary surfaces, and the first and second engagement members 116, 114 each comprise a portion of a hollow cylinder. Consequently, when the complementary surfaces of the first and second engagement members 116, 114 engage one another as shown in FIG. 1B, a hollow cylinder is formed.

In one embodiment, a delivery system like that shown in FIG. 1B may be employed to place the implantable device 106 at a target site within the vasculature using a catheter. Once the catheter has been guided to the desired location in the vasculature, the distal end of the coil (not shown in FIG. 1B) is placed into a proximal open end of the catheter and advanced through the catheter via the delivery member 112. Once the implantable device 106 emerges from the distal end of the catheter and is positioned at the desired target site, the activation wire 109 can be withdrawn, allowing the first engagement portion 110 to decouple from the second engagement portion 104, thereby releasing the medical device 106 at the vascular site. Because the first engagement portion 110 is designed such that essentially all of the proximal-facing surface area of the first engagement portion 110 is angled away from the proximal end of the first engagement portion 110, withdrawal of the first engagement portion from the vasculature and into the catheter is facilitated.

In various additional embodiments, the first engagement portion is provided with a proximal-facing surface that may comprise, for example, a partial surface of a spheroid (e.g., a sphere, oblate spheroid, prolate spheroid, etc.). In some of these embodiments, the first engagement portion may comprises a spheroid or a portion thereof (e.g., a hemi-spheroid such as a hemisphere) wherein the spheroid or a portion thereof contains the first lumen of the first engagement portion. As discuss in more detail below, the elongated delivery member may be directly or indirectly attached to a circumference of the spheroid.

Figure 2A:
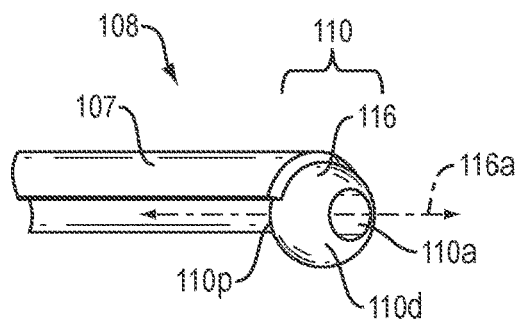
FIG. 2A is a schematic illustration of a distal portion of a delivery device in accordance with an embodiment of the present disclosure.
Figure 2B:
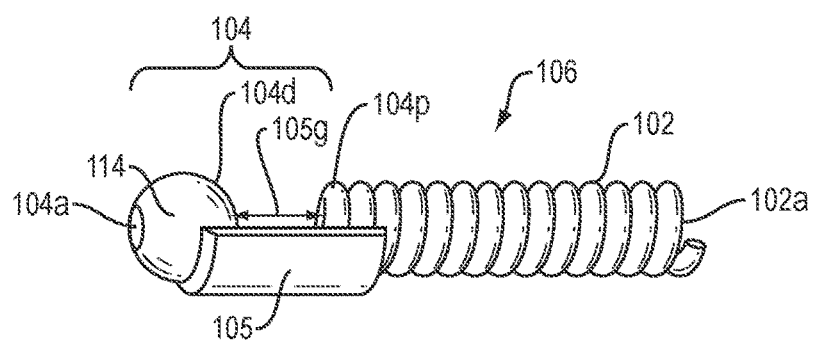
FIG. 2B is a schematic illustration of a proximal portion of a delivery device in accordance with an embodiment of the present disclosure.
Figure 2C:
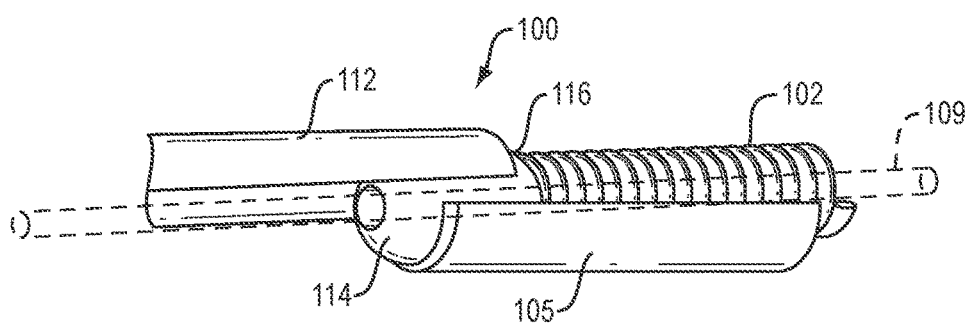
FIG. 2C is a schematic illustration of a delivery system wherein the delivery device of FIG. 2A and the implantable device of FIG. 2B are coupled and held together via an actuation wire.

Turning now to FIGS. 2A-2C, and in particular to FIGS. 2A and 2B, there are schematically illustrated therein a distal portion of a delivery device 108 and a proximal portion of an implantable device 106, respectively. The distal portion of the delivery device 108 comprises a first engagement portion 110 comprising a first lumen 110*a*, a first proximal-facing surface 110*p* and a first distal-facing surface 110*d*, wherein substantially all of the proximal-facing surface area of the first engagement portion 110 (i.e., corresponding to the area of first proximal-facing surface 110*p*) is angled away from the proximal end of the delivery device. In the example shown, the first proximal-facing surface is a curved surface and, more particularly, is a portion of a spherical surface. A surface of this type is advantageous in that, when the delivery device 108 is ultimately withdrawn proximally after delivery of the implantable device, it is less likely to engage another object (e.g., tissue or a previously implanted device). In the particular embodiment shown, the first lumen 110*a* and surfaces 110*p*, 110*d* are provided by a first engagement member 116, which is in the form of a sphere having a lumen 110*a* with an axis 116*a*. FIG. 2A also includes an attachment member 107 that is attached to the first engagement member 116 and is discussed in more detail below.

The implantable device 106 includes a medical device portion, for example, an occlusion device such as an embolization coil 102 having a coil lumen (only a proximal portion of the embolization coil is illustrated) and a second engagement portion 104 comprising a second lumen 104*a*, at least one second distal-facing surface 104*d* and at least one second proximal-facing surface 104*p*. The second lumen 104*a* and the second distal-facing surface 104*d* are provided by a second engagement member 114, which is in the shape of a sphere having a lumen formed therein. The second proximal-facing surface 104*p* is provided by coil 102. The second engagement member 114 and coil 102 are held a fixed distance apart by spacing member 105, forming a gap 105*g*.

Prior to delivery, first and second engagement portions 110, 104 are bought together as shown in FIG. 2C. (It is noted that the spacing member 105 in the embodiment shown in FIG. 2C is longer than the spacing member 105 in the embodiment shown in FIG. 2B.) Specifically, the first engagement member 116 of the delivery device is introduced into the gap 105*g* of the implantable device. Beneficially, a width of the gap is wider than a diameter of first engagement member 116 by an amount that is just sufficient to allow first engagement member 116 to be readily released. Once the first and second engagement portions 110, 104 are bought together as shown, an activation wire 109 (a portion of which is shown in phantom) is simultaneously positioned within the first and second lumens 110*a*, 104*a* such that the delivery device and implantable device are reversibly coupled. In particular, the activation wire 109 simultaneously occupies the first engagement portion lumen 110*a*, the second engagement portion lumen 104*a*, and a portion of a coil lumen 102*a* (although not required for coupling). Because the first engagement portion 110 has at least one proximal-facing surface 110*p* that faces at least one distal-facing surface 104*d* of the second engagement portion 104, when the delivery device 108 is pulled in a proximal direction, the first engagement portion 110 will engage and pull the second engagement portion 104 in a proximal direction. Analogously, because the first engagement portion 110 has at least one distal-facing surface 110*d* that faces at least one proximal-facing surface 104*p* of the second engagement portion 104, when the delivery device 108 is pushed in a proximal direction, the first engagement portion 110 will engage and push the second engagement portion 104 in a proximal direction.

Once the first and second engagement portions 110, 104 are paired as shown in FIG. 2C and the activation wire 109 is introduced through the lumens 110*a* and 104*a* of the first and second engagement portions 110, 104, then first and second engagement portions 110, 104 will remained coupled until the activation wire 109 is removed, at which point the first and second engagement portions 110, 104 are released from one another.

As will be appreciated by those of ordinary skill in the art upon viewing FIGS. 2A-2C, the attachment member 107 is beneficially attached along portion of a circumference of the first engagement member 116 that lies on a plane that is normal to axis 116*a* so as to allow the first engagement member 116 to be introduced into gap 105*g* without interference from the attachment member 107. The attachment member 107 shown comprises a section of a hollow cylinder, for example, which may correspond to a distal portion of a tubular delivery member from which material has been cut away, or which may be attached to a separate elongated delivery member (not shown). Moreover, many other geometries may be employed for the attachment member. For example, the attachment member 107 may be in the form of a thin stiff wire (e.g. a curved or straight ribbon-shaped wire, among others) in some embodiments. In addition, although the coil 102 provides the proximal-facing surface 104*p* of the second engagement portion 104 in the embodiment shown, a separate engagement member may be provided for this purpose. Moreover, although the distal-facing surface 104*d* of the second engagement portion 104 is provided by a second engagement member 114 in the shape of a spheroid in the embodiment shown, second engagement members of myriad other geometries may be may be employed to provide the distal-facing surface 104*d*, so long as the geometry also allows insertion of the activation wire 116 and allows for release of the first engagement portion 110. Furthermore, although the second lumen 104*a* is provided by the second engagement member 114, this function may be provided by the coil 102 or an attachment thereto.

In one embodiment, a delivery system like that shown in FIG. 2C may be employed to place the implantable device 106 at a target site within the vasculature using a catheter. Once the catheter has been guided to the desired location in the vasculature, the distal end of the coil (not shown) may be placed into a proximal open end of the catheter and advanced through the catheter via the delivery member. Once the implantable device 106 emerges from the distal end of the catheter and is positioned at the desired target site, the activation wire 109 can be withdrawn, allowing the first engagement portions 110 to decouple from the second engagement portion 104 to disengage, thereby releasing the medical device 106 at the vascular site. Because the first engagement portion 110 is designed such that essentially all of the proximal-facing surface area of the first engagement portion 110 is angled away from the proximal end of the first engagement portion 110, withdrawal of the first engagement portion from the vasculature and into the catheter is facilitated.

Although specific embodiments have been described with an embolic coil in the drawings, one of ordinary skill in the art will appreciate that variety of alternative medical devices could be substituted. For example, the systems described herein may be used to deliver a variety of implantable devices in addition, or as an alternative, to the embolic coil (e.g., scaffolding, therapeutic drugs, thrombogenic embolizing agents, etc.). Similarly, a variety of control devices for moving an implantable device through a lumen of a medical instrument may be employed as a delivery member.

Still further, while the delivery system is generally described with respect to the detachable device traveling through a catheter, one skilled in the art will appreciate that the device may travel through a variety of medical instruments, such as, for example, introducers or endoscopes, and that the methods and devices describe herein are equally applicable to any medical device having a lumen for the delivery of a detachable, implantable device. In this regard, the term "catheter" as used herein can refer to the variety of medical devices having an inner lumen adapted for receiving a medical instrument and/or implantable device.

Still other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A medical delivery system comprising:
   (a) a delivery device comprising an elongated delivery member and a first engagement portion comprising a first proximal-facing surface having at least a portion of a surface area angled away from a proximal end of the first engagement portion, a first distal-facing surface that faces away from the delivery device, a second distal-facing surface extending away from the first proximal-facing surface, and a first lumen that is configured to accommodate an activation wire;
   (b) an implantable device comprising a medical device portion and a second engagement portion comprising a second lumen, a first proximal-facing surface, a second proximal-facing surface and a first distal-facing surface, and
   (c) an activation wire,
   wherein the activation wire is configured to simultaneously occupy the first and second lumens thereby holding the first and second engagement portions in a coupled state, in which the first distal-facing surface of the first engagement portion engages the first proximal-facing surface of the second engagement portion, and the second distal-facing surface of the first engagement portion engages the second proximal facing surface of the second engagement portion, when the medical device portion is pushed distally by the elongated delivery member, and in which the first proximal-facing surface of the first engagement portion engages the first distal-facing surface of the second engagement portion, when the medical device portion is pulled proximally by the elongated delivery member, and wherein the activation wire is configured to be removed from the first and second lumens thereby releasing the first and second engagement portions from the coupled state; and wherein the first proximal-facing surface of the first engagement portion is between the first distal-facing surface and the second distal-facing surface of the first engagement portion.

2. The medical delivery system of claim 1, wherein the medical device portion comprises a vascular occlusion device.

3. The medical delivery system of claim 1, wherein the medical device portion comprises an embolic coil.

4. The medical delivery system of claim 1, wherein the first and second engagement portions comprise complementary surfaces.

5. The medical delivery system of claim 1, wherein the first and second engagement portions each comprises a portion of a hollow cylinder.

6. The medical delivery system of claim 1, wherein the first and second engagement portions form a hollow cylinder in the coupled state.

7. A method of implanting an implantable device in a subject comprising inserting a medical system in accordance with claim 1 into the subject when in said coupled state and withdrawing the activation wire from the first and second lumens such that the implantable device is released in said subject.

8. The medical delivery system of claim 1, wherein at least a portion of a surface area of the first distal-facing surface of the second engagement portion is angled away from a distal end of the second engagement portion.

9. The medical delivery system of claim 8, wherein the at least the portion of the surface area of the first distal-facing surface of the second engagement portion is at least 50% of the surface area of the first distal-facing surface.

* * * * *